(12) United States Patent
Hall et al.

(10) Patent No.: US 9,125,782 B2
(45) Date of Patent: Sep. 8, 2015

(54) SURGICAL TABLE

(71) Applicant: Stille AB, Solna (SE)

(72) Inventors: Leif Hall, Norsborg (SE); Elin Rondahl, Sundbyberg (SE)

(73) Assignee: Stille AB, Solna (SE)

( * ) Notice: Subject to any disclaimer, the term of this patent is extended or adjusted under 35 U.S.C. 154(b) by 0 days.

(21) Appl. No.: 14/512,483

(22) Filed: Oct. 13, 2014

(65) Prior Publication Data

US 2015/0059092 A1   Mar. 5, 2015

Related U.S. Application Data

(63) Continuation of application No. PCT/SE2013/050396, filed on Apr. 12, 2013.

(30) Foreign Application Priority Data

Apr. 13, 2012  (SE) .................................. 1250370-2

(51) Int. Cl.
| | | |
|---|---|---|
| *A61G 13/02* | (2006.01) | |
| *A61B 6/04* | (2006.01) | |
| *A61G 13/12* | (2006.01) | |

(52) U.S. Cl.
CPC . *A61G 13/02* (2013.01); *A61B 6/04* (2013.01); *A61G 13/129* (2013.01); *A61G 2200/16* (2013.01)

(58) Field of Classification Search
CPC ...... A61B 6/04; A61B 6/0407; A61B 5/0555; A61B 5/055; A61G 7/00; A61G 7/002; A61G 7/005; A61G 13/00; A61G 13/02; A61G 13/04; A47B 13/081
USPC ...................... 5/600, 601, 943; 378/208, 209; 108/137, 143
See application file for complete search history.

(56) References Cited

U.S. PATENT DOCUMENTS

| | | | | |
|---|---|---|---|---|
| 307,962 | A * | 11/1884 | Kossbiel | 108/5 |
| 3,643,604 | A * | 2/1972 | Jones et al. | 108/5 |
| 3,814,414 | A * | 6/1974 | Chapa | 5/601 |
| 4,475,072 | A | 10/1984 | Schwehr et al. | |
| 4,700,938 | A * | 10/1987 | Chambron | 5/601 |
| 5,263,384 | A * | 11/1993 | Suzuki | 74/490.13 |
| 5,533,844 | A * | 7/1996 | Ekleberry | 409/159 |
| 6,416,219 | B1 | 7/2002 | Pflaum et al. | |
| 6,769,145 | B1 * | 8/2004 | Pfeuffer et al. | 5/601 |
| 8,918,933 | B2 * | 12/2014 | Holden et al. | 5/655 |
| 2006/0293589 | A1 | 12/2006 | Calderon et al. | |
| 2013/0025064 | A1 * | 1/2013 | Holden et al. | 5/655 |
| 2015/0026889 | A1 * | 1/2015 | Roselius et al. | 5/601 |
| 2015/0059092 | A1 * | 3/2015 | Hall et al. | 5/600 |

FOREIGN PATENT DOCUMENTS

WO    WO0211618    2/2002

* cited by examiner

*Primary Examiner* — Robert G Santos
(74) *Attorney, Agent, or Firm* — Bergenstrahle & Partners AB; Gabriela B. Tomescu, Esq.

(57) ABSTRACT

A surgical table having a table top for receiving a patient thereon, a support for supporting the table top, two rails connected to the table top one on each side in the direction of the longitudinal axis of the table top, and at least one slide means on each side of the support for slidingly receiving the rail along the longitudinal axis. The rails are connected to the table top at two connection points on each side of the table top or is connected to the table top at one connection point only and the other end of the table top lies on a pin that may be joined in the corresponding connection point on each side of the table top.

5 Claims, 3 Drawing Sheets

SURGICAL TABLE

This application is a continuation of PCT Application No. PCT/SE2013/050396, filed Apr. 12, 2013, which claims priority of SE 1250370-2, filed Apr. 13, 2012, the entire contents of each of which are hereby incorporated by reference.

TECHNICAL FIELD

The present invention relates generally to surgical tables, and more particularly to a surgical table with a movable table top.

BACKGROUND ART

Some surgical tables are previously known and many of them are individually movable, wherein a table top is movable along a vertical and a horizontal axis. The table top is in many surgical tables attached to a support in one end so that a remainder of the table top hangs freely. This design is particularly important when it comes to those requiring the use of for example a mobile C-arm. The table top may be movable along the longitudinal axis by means of two side rails running in slides at the support. The side rails are attached along the sides of the table top, either continuously or intermittently along the length of the rails.

One problem with these surgical tables is that the table top bends when a person lies on it, especially if the person is heavy. When the table top is bent, the side rails are also affected by the bending forces which make the rails to bend, too. This counteracts the movement of the table top since the slide means receiving the rail in a slidably manner during movement of the table top cannot receive the bent rail freely slidable and gets jammed. In order to overcome the risk of jamming the slides, articulated slides are used, but a resistance remains.

This poses some problems, especially for the personnel due to the resistance to move the table top lengthwise and the difficulty to position the table top in the exact required position.

SUMMARY OF INVENTION

An object of the present invention is to provide a surgical table having an easy and exact positioning of the table top, preferably giving a feeling of floating when moving the table top.

According to a general embodiment of the invention a surgical table comprises a movable table top for receiving a patient thereon, wherein the table top is supported by a support in one end thereof. Two rails are connected, one on each side, to each side of the table top in the direction of the longitudinal axis of the table top. The rails slide along the length axis through slide means, and there is at least one slide means on each side of the support for receiving the rail. The rails are connected to the table top at one or two connection points on each side.

In one embodiment the rails are connected to the table top at two connection points (7a, 7b) on each side of the table top or is connected to the table top (2) at one connection point only (7a) and the other end of the table top (2b) lies on a pin that may be joined in the corresponding connection point (7b) on each side of the table top.

In one embodiment the table top has a first connection point of one rail situated in the same end as the support and a second connection point situated in the vicinity of the other end of the rail.

In another embodiment, each rail is connected to the table top at one connection point only, and preferably at a first end portion of the table top which is supported by the support.

In another embodiment the table top has a first connection point of one rail on one side aligned with a first connection point of the rail on the other side through an orthogonal axis to the length axis of the table top.

In yet another embodiment the table top is rotatably connected about the connection points which further decrease the bending forces on the rails originating from the table top.

In one embodiment each of the first and/or second connection point(s) comprises a pin. In another embodiment the pin may be rotatable inside a receiving holder or recess.

In yet another embodiment of the table top the first connection point is in the same end as the support and the second connection point is separated from the first connection point with about 0.50 to 1.50 m. In another embodiment the distance between the connection points is long enough to reduce the bending forces originating from the loaded table top but situated in each end of the rail.

The present invention provides a solution that counteracts the establishment of the bending forces from the bent table top to the rails, thereby facilitating the sliding movement of the rails through the slide means. This allows the movements in the length axis to float in a very smooth way.

BRIEF DESCRIPTION OF DRAWINGS

The invention is now described, by way of example, with reference to the accompanying drawings, in which.

DESCRIPTION OF EMBODIMENTS

Before the invention is disclosed and described in detail, it is to be understood that this invention is not limited to particular materials or configurations disclosed herein as such configurations and materials may vary. It is also to be understood that the terminology employed herein is used for the purpose of describing particular embodiments only and is not intended to be limiting since the scope of the present invention is limited only by the appended claims.

The present invention will now be described in more detail hereafter with reference to the accompanying figures, in which embodiments of the invention are shown. This invention may, however, be embodied in many different forms and should not be construed as limited to the embodiments set forth herein.

Figure 1:
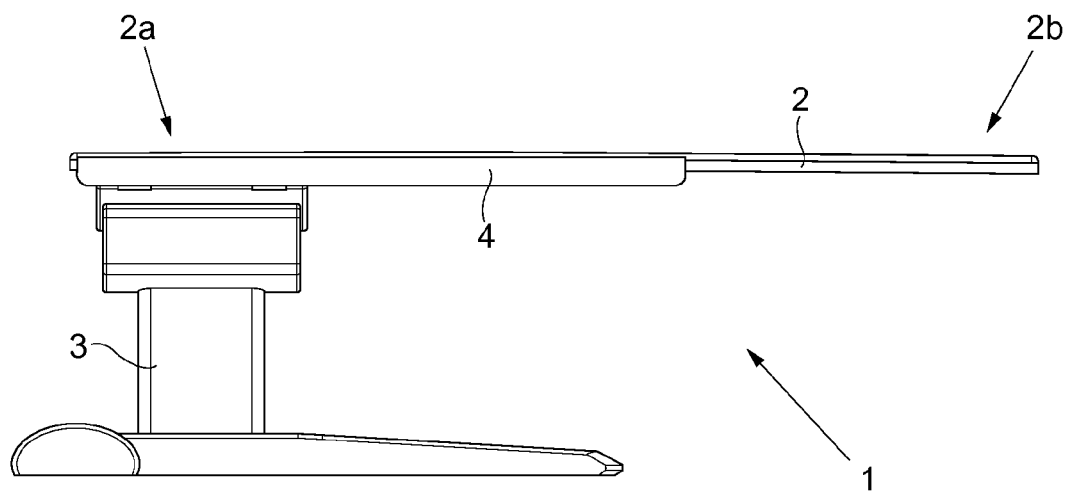
FIG. 1 shows a side view of a surgical table in an unloaded position.
Figure 2:
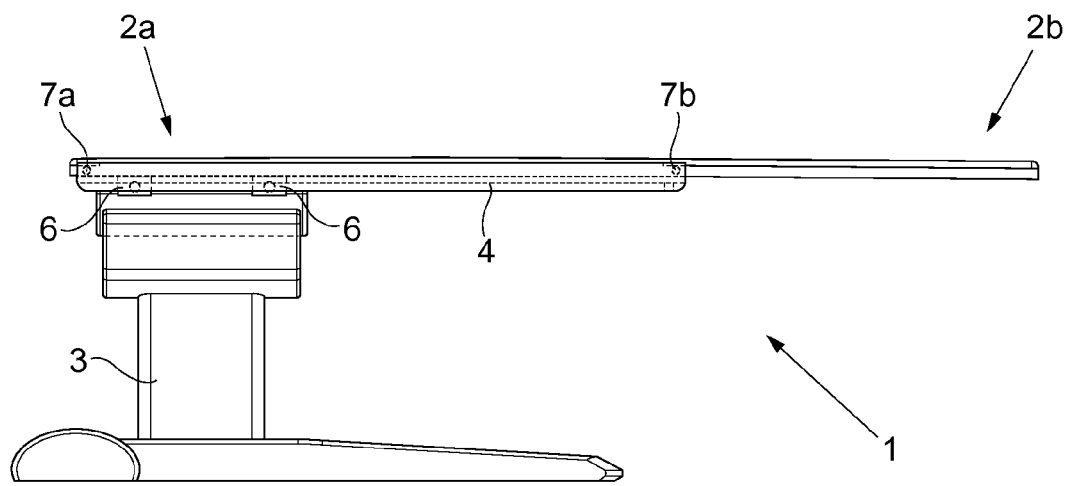
FIG. 2 show a sectional side view of the surgical table of FIG. 1.

FIGS. 1 and 2 show a side view of a surgical table 1, wherein in FIG. 1 some of the interior parts are also shown. The surgical table 1 comprises a table top 2 which in these figures are shown without the influence of a patient's weight. The table top 2 has two end portions, namely a first end portion 2a which is supported by a support 3, and a second end portion 2b which is free, i.e., is not directly supported by the support. A rail 4 is connected to the table top 2 on each side thereof in one or two connection points 7a, 7b, see FIG. 2. This embodiment has two connection points; the first connection point 7a is in the same end of the rail 4 as the supported first end portion 2a of the table top 2, and the second connection point 7b is in the other end of the rail 4 closer to the free second end portion 2b of the table top 2. The rails 4 may comprise connection means in the form of pre made holes so that the rails 4 are connectable to the table top 2 by means of pins, as will be described below. The table top 2 comprises in turn the corresponding predetermined connection means that the connection to the rails 4 requires. This embodiment show a rail 4 with pre-made holes connected to the bed via pins. The connection may be fixed or rotatable around an axle. The rails 4 extend partly along the length of the table top 2. The surgical table 1 has in this embodiment two slide means 6 on each side of the support 3 for slidingly receiving the rail 4 along the length of the table top 2.

At least one clamping or locking element (not shown) is adapted to block the sliding movement of the rails 4 thereby locking the table top 2 in a desired longitudinal position.

The rails 4 on each side of the table top 2 are less influenced by the bending of the table top 2 due to free rotation around pins in the connection points 7.

Figure 3:
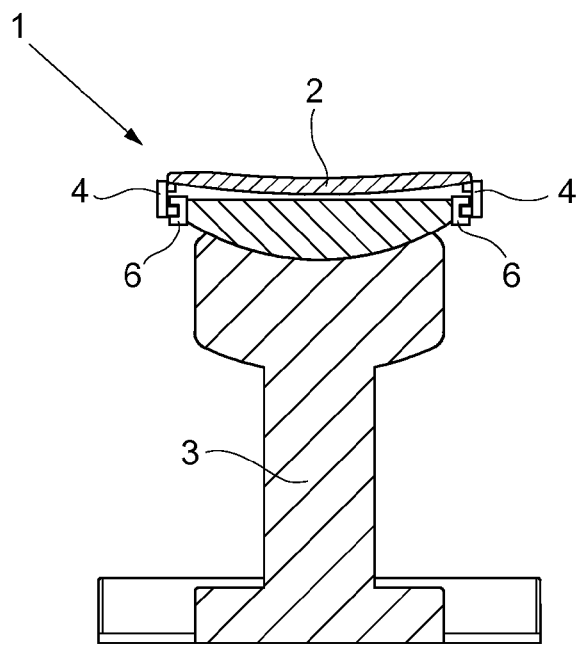
FIG. 3 shows a cross sectional view of the present surgical table.

FIG. 3 shows the surgical table 1 in a cross sectional view from the free end 2b of the table top 2. The somewhat U-shaped table top 2 is supported by the support 3 and connected to the rails 4 on each side. The rails 4 on each side of the table top 2 are slidably movable in the slide means 6 along the length of the table top. The rails 4 on each side are connected to the table top 2 via pins inserted into the connection points 7 from the external side received of an adapted recess or nut. The pins may be rotatable 360 degrees inside respective connection point 7 further decreasing the bending forces on the rails 4.

Figure 4:
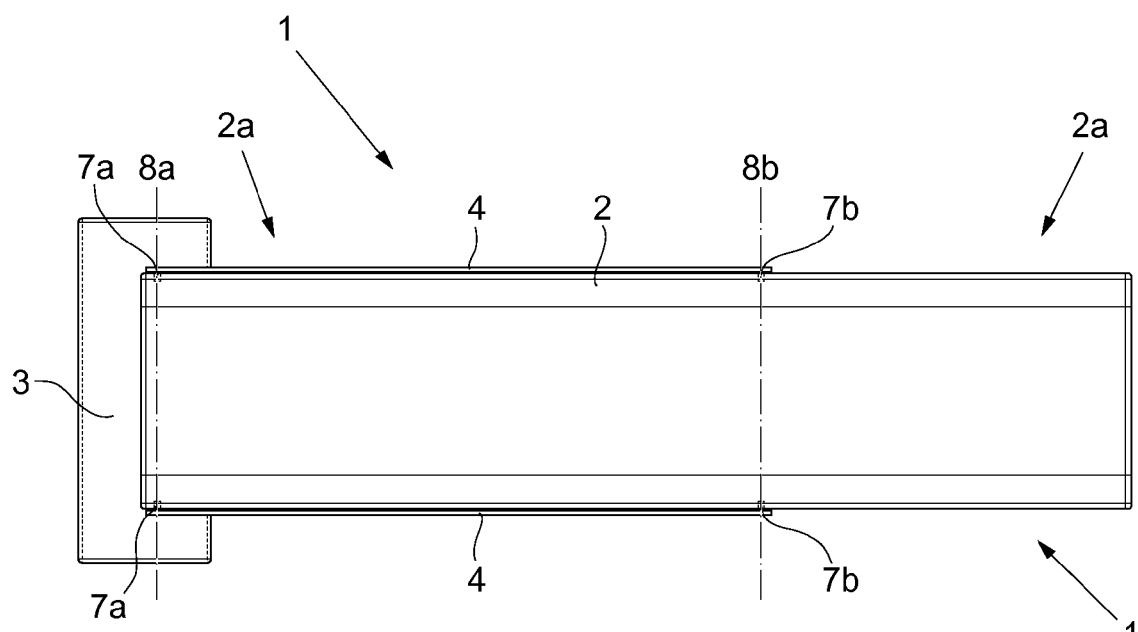
FIG. 4 shows a top view of the present surgical table.

FIG. 4 shows a top view of the table top 2 having the supported end portion 2a on the left side and the free end portion 2b on the right side of the drawing. The rails 4 extend only partly along the length of the table top 2. One connection point 7a supports one end of a respective rail 4, and the other connection point 7b supports the other end of a respective rail 4. The second connection point 7b of each rail 4 is at a distance long enough to move the bending force further away from the support 3. This solution moves the second connection point 7b closer to the free end portion 2b of the table top, which means that a smaller length is prone to bend because of a heavy patient. The connection points 7a, 7b in the first and second ends of each of the rails 4 are provided at the same distance along the table top 2 on the two sides thereof. This means that the connection points 7a at the supported first end portion 2a of the table top 2 are aligned with each other along a virtual first axis 8a, which means that the table top 2 is rotatable about this first axis 8a. Similarly, the connection points 7b at the free second end portion 2b of the table top 2 are aligned with each other along a virtual second axis 8b, which means that the table top 2 may be rotatable also about this second axis 8b.

Figure 5:
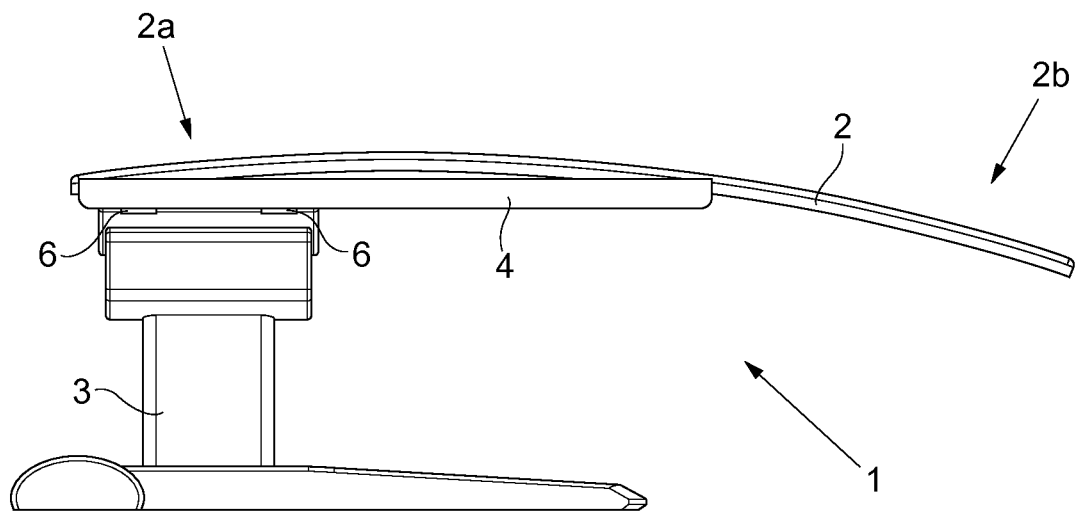
FIG. 5 shows a side view of the surgical table shown in FIGS. 1-4 but in a loaded position.

FIG. 5 shows a side view of the same surgical table 1 as in the previous figures, but in a somewhat exaggerated view when a heavy patient is positioned on the table top. Due to the heavy weight distributed along the table top 2, a bending effect will form and the table top 2 will bend down as shown in the drawing. The bending mechanism of the table top 2 can be compared to the trampoline principle, where the free end over the water bends due to a person's weight. When the table top 2 is bent by the bend forces, the bend forces will be transmitted to the rails 4. The rails 4 will be less influenced by the bending forces due to that they are connected to the table top in only a first and a second connection point 7a, 7b situated in its both ends.

However, since each rail 4 is connected to the table top in only two connecting points 7a, 7b on each side, the rails 4 are almost unaffected by the bent table top 2, which in turn enables the rails 4 to slide smoothly in the slide means 6 without jamming. This allows the movements in the length axis to float in a very smooth way.

Figure 6:
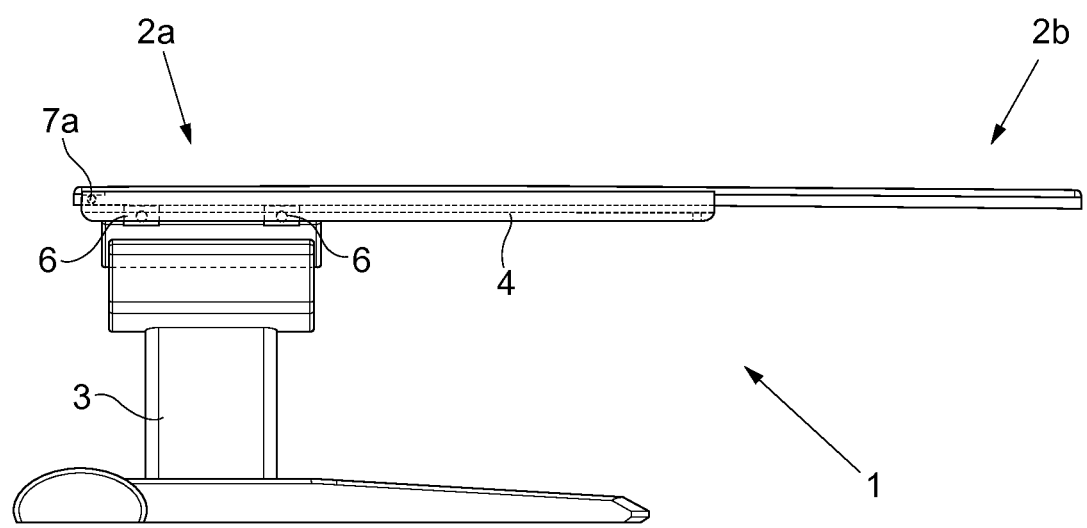
FIG. 6 shows a sectional side view of a second embodiment of a surgical table similar to that of FIGS. 1-5 but wherein the table top is attached in only one point at each side of the table top.

FIG. 6 shows a second embodiment of a surgical table wherein the table top 2 is connected to the rail 4 in only the first connection point 7a on each side. The table top 2 lies on a pin that may be joined in the corresponding connection points 7b. In all other aspects this second embodiment is identical to the first embodiment described above with reference to FIGS. 1-5 and reference to these figures are made for understanding this second embodiment.

Finally, the present invention provides a solution that counteracts the establishment of the bending forces from the bent table top 2 to the rails 4, thereby facilitating the sliding movement of the rails through the slide means 6. This allows the movements in the length axis to float in a very smooth way.

Other features and uses of the invention and their associated advantages will be evident to a person skilled in the art upon reading the description and the examples. Thus, the connections means provided to interconnect the table top and the rails can be any suitable means allowing the table top to take on a bent shape when the weight of a patient exerts a pressure on the top of the table top. For example, the table top can be provided with brackets on the underside thereof adapted to receive a shaft extending perpendicularly to the longitudinal direction of the table top, wherein the shaft is attached to the two rails.

The invention claimed is:

1. A surgical table having a table top for receiving a patient thereon, a support for supporting the table top, two rails connected to the table top one on each side in the direction of the longitudinal axis of the table top, and at least one slide means on each side of the support for slidingly receiving the rail along the longitudinal axis, wherein the rails are connected to the table top at two connection points on each side of the table top or is connected to the table top at one connection point only and the other end of the table top lies on a pin that may be joined in the corresponding connection point on each side of the table top, a first connection point of one rail on one side is aligned with a first connection point of the rail on the other side through an orthogonal axis to the length axis, and wherein the table top is rotatably connected around said connection points.

2. The surgical table according to claim 1, wherein a first connection point of one rail is situated in an end of the rail aligned with the support and a second connection point is situated in the other end of the rail.

3. The surgical table according to claim 1, wherein each of the first and/or second connection points comprise a pin.

4. The surgical table according to claim 1, wherein the first connection point is in the same end as the support and wherein the second connection point is separated from the first connection point with about 0.50 to 1.50 m.

5. The surgical table according to claim 4, wherein each rail is connected to the table top at a first end portion thereof which is supported by the support.

* * * * *